United States Patent
Rebuffat et al.

(10) Patent No.: US 8,740,781 B2
(45) Date of Patent: *Jun. 3, 2014

(54) ANOSCOPE FOR ANO-RECTAL DIAGNOSTIC AND SURGERY

(71) Applicants: Covidien AG, Neuhausen am Rheinfall (CH); Piera Rebuffat; Franca Rebuffat

(72) Inventors: Carlo Rebuffat, Carate Brianza (IT); Dante David, Cologno Monzese (IT); Ricardo Rosati, Milan (IT)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/675,366

(22) Filed: Nov. 13, 2012

(65) Prior Publication Data
US 2013/0150682 A1 Jun. 13, 2013

Related U.S. Application Data

(63) Continuation of application No. 12/090,345, filed as application No. PCT/IT2005/000619 on Oct. 26, 2005, now Pat. No. 8,337,401.

(51) Int. Cl.
*A61B 1/00* (2006.01)

(52) U.S. Cl.
USPC .......................................... 600/184; 606/197

(58) Field of Classification Search
USPC ................ 606/108, 184, 191, 197; 604/264; 600/184, 185, 186, 201, 202, 203, 204, 600/205; 128/200.24, 200.26
See application file for complete search history.

(56) References Cited

U.S. PATENT DOCUMENTS

| | | | |
|---|---|---|---|
| 295,798 | A | 3/1884 | Pagett |
| 314,132 | A | 3/1885 | Ingersoll |
| 357,216 | A | 2/1887 | McCall |
| 457,787 | A | 8/1891 | Leisenring |
| 2,290,571 | A | 7/1942 | Peyton |
| 2,469,880 | A | 5/1949 | Kowan |
| 2,754,822 | A | 7/1956 | Emelock |

(Continued)

FOREIGN PATENT DOCUMENTS

| | | |
|---|---|---|
| DE | 3717607 | 12/1988 |
| EP | 1929959 | 11/2008 |
| WO | WO2009/092194 | 7/2009 |

OTHER PUBLICATIONS

PCT International Search Report for PCT/IT2005/000619 filed Oct. 26, 2005 in the name of Carlo Rebuffat, et al.

(Continued)

*Primary Examiner* — Ryan Severson
*Assistant Examiner* — Jonathan W Miles

(57) ABSTRACT

A composite anoscope for ano-rectal diagnostic and surgery, wherein the anoscope (2) also comprises an internal component (1), to be inserted therein, and a suitably shorter external component (3), ending with a conic frustum mantle (18), wherein the anoscope (2) is to be inserted. The three components (1, 2, 3) are all conic frustum shaped hollow bodies having circular cross-section. The internal component (1), when inserted in the anoscope (2), forms therewith a single body having a compact and smooth external surface and an ogival tip. The external component (3) is provided close to its mouth with slotted wings (19, 20), to be fixed to the perianal skin for securing the whole composite anoscope during the diagnostic and surgical operations.

35 Claims, 2 Drawing Sheets

(56) References Cited

U.S. PATENT DOCUMENTS

| | | |
|---|---|---|
| 2,769,441 A | 11/1956 | Abramson |
| 2,922,415 A | 1/1960 | Campagna |
| 3,051,176 A | 8/1962 | Albertl et al. |
| 3,132,645 A | 5/1964 | Gasper et al. |
| 3,459,175 A | 8/1969 | Miller |
| 3,701,347 A | 10/1972 | Belkin |
| 4,220,155 A | 9/1980 | Kimberling et al. |
| 4,341,211 A | 7/1982 | Kline |
| 4,834,067 A | 5/1989 | Block et al. |
| 4,957,499 A | 9/1990 | Lipatov et al. |
| 5,122,149 A | 6/1992 | Broome |
| 5,176,127 A | 1/1993 | Dormia |
| 5,256,149 A | 10/1993 | Banik et al. |
| 5,351,674 A | 10/1994 | Hawks |
| D353,197 S | 12/1994 | Hawks |
| 5,404,870 A | 4/1995 | Brinkerhoff et al. |
| 5,425,736 A | 6/1995 | Wadworth |
| D360,261 S | 7/1995 | Swanson et al. |
| 5,464,412 A | 11/1995 | Budding et al. |
| 5,509,893 A | 4/1996 | Pracas |
| D384,412 S | 9/1997 | Mainiero |
| 5,716,329 A | 2/1998 | Dieter |
| 5,741,273 A | 4/1998 | O'Regan |
| 5,916,150 A | 6/1999 | Sillman |
| 5,931,776 A | 8/1999 | Dotolo |
| 5,957,902 A | 9/1999 | Teves |
| 6,083,241 A | 7/2000 | Longo et al. |
| 6,102,271 A | 8/2000 | Longo et al. |
| 6,126,594 A | 10/2000 | Bayer et al. |
| 6,136,009 A | 10/2000 | Mears |
| 6,142,933 A | 11/2000 | Longo et al. |
| 6,152,936 A | 11/2000 | Christy et al. |
| 6,428,473 B1 | 8/2002 | Leonard et al. |
| 6,497,654 B1 | 12/2002 | Leonard et al. |
| 6,503,192 B1 | 1/2003 | Ouchi |
| 6,506,157 B1 | 1/2003 | Teigman et al. |
| 6,547,798 B1 | 4/2003 | Yoon et al. |
| 6,616,603 B1 | 9/2003 | Fontana |
| 6,702,741 B2 | 3/2004 | Rioux et al. |
| 6,740,098 B2 | 5/2004 | Abrams et al. |
| 6,740,101 B2 | 5/2004 | Houser et al. |
| 6,761,687 B1 | 7/2004 | Doshi et al. |
| 7,029,438 B2 | 4/2006 | Morin et al. |
| 7,037,314 B2 | 5/2006 | Armstrong |
| D564,657 S | 3/2008 | Tsai |
| 7,452,329 B2 | 11/2008 | Bastia et al. |
| 7,611,458 B2 | 11/2009 | Sias |
| 8,337,401 B2 * | 12/2012 | Rebuffat et al. .............. 600/184 |
| 2003/0069472 A1 | 4/2003 | Bulter |
| 2003/0130559 A1 | 7/2003 | Morin et al. |
| 2004/0260152 A1 | 12/2004 | Sant et al. |
| 2005/0277811 A1 | 12/2005 | Richards et al. |
| 2006/0009797 A1 | 1/2006 | Armstrong |
| 2006/0036129 A1 | 2/2006 | Sias |
| 2006/0212046 A1 | 9/2006 | Pearce et al. |
| 2007/0043264 A1 | 2/2007 | Gillis et al. |
| 2008/0091218 A1 | 4/2008 | Richardson |
| 2008/0097478 A1 | 4/2008 | Doughty et al. |
| 2008/0262511 A1 | 10/2008 | Delaney |
| 2009/0005647 A1 | 1/2009 | Bozdag |
| 2009/0012356 A1 | 1/2009 | Dann et al. |

OTHER PUBLICATIONS

International Search Report for PCT/IT2005/000619 date of completion is Jun. 21, 2006 (3 pages).

* cited by examiner

ANOSCOPE FOR ANO-RECTAL DIAGNOSTIC AND SURGERY

CROSS-REFERENCE TO RELATED APPLICATIONS

The present application is a continuation of U.S. patent application Ser. No. 12/090,345, filed on Apr. 15, 2008, which is a National Stage Entry under 35 U.S.C. §371(a) of International Patent Application No. PCT/IT2005/000619, filed on Oct. 26, 2005, the entire contents of each of the above-identified applications being incorporated by reference herein.

The present invention generally relates to an anoscope for ano-rectal diagnostic and surgery and particularly to a composite anoscope consisting of three conic frustum shaped components to be inserted one in each other.

Anoscopes are surgical instruments used for exploring the anal canal and the lower third portion of the rectum. Anoscopes usually are cylindrical pipes to be introduced in the anal canal by means of an appropriate introduction device. Composite anoscopes are also known, that is, anoscopes associated with one or more components, which, further to exploring the anal canal, permit performing ano-rectal surgery such as hemorrhoidectomy.

From U.S. Pat. No. 6,126,594 is known for example an anoscope which may be combined with another cylindrical component and wherein the latter is to be inserted. Said anoscope is provided with longitudinal slots, which are separated by lamellar protrusions. This geometry allows suturing a plurality of hemorrhoids located about the inner perimeter of the rectal wall. This known anoscope shows many drawbacks, of which one is that its introduction into the anal canal is traumatic because of the protuberance of the lamellar protrusions from the internal component which can damage the adjacent tissues. Furthermore, there is no stable system for positioning and fixing the anoscope when in use.

From U.S. Pat. No. 6,142,933 there is also known a composite anoscope consisting of three components for suturing hemorrhoids when performing hemorrhoidectomy. Also this known anoscope shows some drawbacks, of which one is that it is provided only with a single operative opening. Further, it is susceptible of moving inside the anal canal during the surgery, therefore it doesn't permit determining exactly the position of injuries with respect to the anal margin.

The exact depth of the suture is an essential parameter both when treating hemorrhoids and when treating other ano-rectal pathologies. An operative opening which is too wide, exposes the surgeon to the risk of suturing also the muscular tunica, in addition to the rectal mucosa. The distance of the suture from the anal margin is another essential parameter for this type of surgery. Finally, also the circumferential extension of the suture is very important, in fact in some cases it is necessary to perform 180.degree.-sutures, in other cases 360°-sutures, etc.

The above mentioned known anoscopes do not permit a certain evaluation of the distance from the anal margin and entrust to the skills and expertise of the surgeon the exact performance of the surgery. They do neither allow evaluating exactly the circumferential extension of the sutures, nor allow determining the distance of the sutures from the anal margin, nor permit fixing the anoscope to the anal tissue during the surgery.

Hence, the scope of the present invention is providing a composite anoscope free from the disadvantages mentioned above. Such scope is achieved by the composite anoscope according to the present invention the features of which are specified in claim 1. Further features of this anoscope are specified in the dependent claims.

The anoscope according to the present invention offers the advantage that its three components, when introduced in the anal canal, constitute a conic frustum shaped single body having an ogival tip and a compact and smooth external surface apted to penetrate in the anal canal in a very atraumatic way.

Another advantage offered by the anoscope according to the present invention is that the external component permits fixing the anoscope by suturing it to the perianal skin, so that its positioning is precise and stable during the whole surgery.

Still another advantage of the anoscope according to the present invention is that its internal surface is provided with longitudinal and circumferential markers which provide an exact location of the position of the injuries in the anal canal allowing suturing at the right depth, at the right distance from the anal margin and with the right circumferential extension.

A further advantage of the anoscope according to the present invention is that it is provided with lamellar protrusions, which at the end are curved towards the ogival tip for giving the right support without damage to the rectal mucosa prolapsing above the tip of the anoscope.

These and other advantages of the composite anoscope according to the present invention will be evident to those skilled in the art from the following detailed description of an embodiment thereof with reference to the enclosed drawings wherein.

Figure 1:
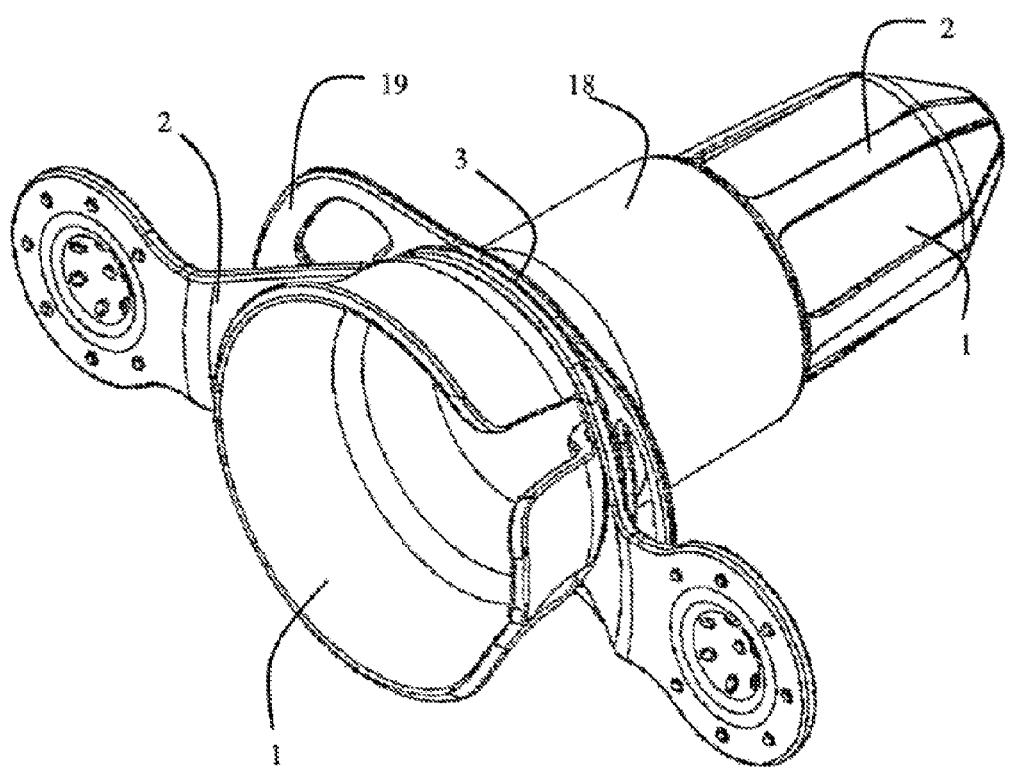
FIG. 1 shows a perspective view of the composite anoscope mounted ready for use, wherein the three components are one inserted inside the other.

FIG. 1, shows that the composite anoscope according to the present invention consists of three hollow conic frustum shaped components which are apted to tightly inserted one in each other so that they form a single body. The geometry and the diametral dimensions of the three components, when these are combined, make the external surface of the instrument smooth and compact allowing in this way above all its easy and atraumatic introduction in the anal canal. The anoscope is the intermediate component 2 in which the internal component 1 is inserted and both of them are axially inserted in the external component 3. Inserting one component in the other in this order is possible because the diameter of external component 3 is slightly larger than the diameter of the anoscope 2, so that the latter can be inserted without play in the external component 3. Similarly, the diameter of component 1 is slightly shorter of the diameter of anoscope 2.

The conicity of the three components permits the reciprocal introduction and extraction of the components without any difficulty, solving the mounting problem which is typical of cylindrical geometries, as seen in one of the anoscope of the prior art.

FIG. 1 shows that the ogival tip of the composite anoscope according to the present invention is the result of the peculiar fitting of the cut off ogival tip of anoscope 2 together with the underlying complete ogival tip of component 1. As it will be explained in detail later, the dimensions and the geometry of the ogival tips of the anoscope 2 and of the internal component 1 are conceived for creating a system of hollow and solid features which become integral to each other when mounted, forming a single body, having smooth and compact external surface, thereby solving one of the problems at the basis of the present invention.

Figure 2:
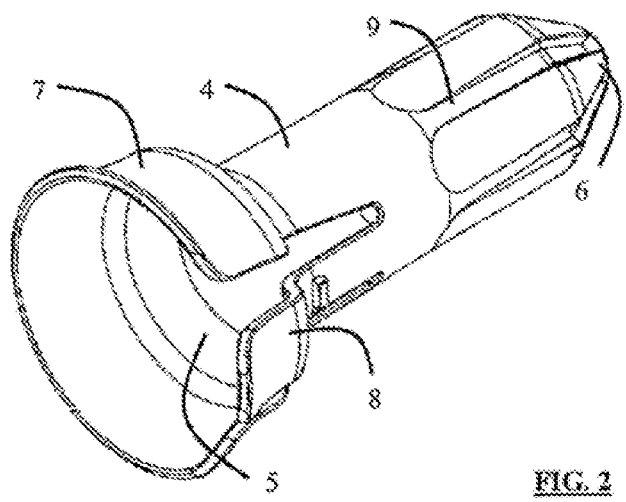
FIG. 2 shows a perspective view of the internal component.

FIG. 2 shows that the component 1 consists of a hollow conic frustum shaped body having attached to the mouth a flange 5, a mantle 4 and an ogival tip 6 at the opposite end. The flange 5 is provided with a handle 7 which permits handling the component 1 correctly, both when mounting the composite anoscope according to the present component and during its use in anoscopy and in other surgical operations. In the present embodiment, the internal component 1 is provided with a snapping tongue device 8, forming in this way a single body with the anoscope 2.

The conic frustum shaped body of the component 1 is provided with a set of parallel longitudinal grooves 9, radially placed and equidistant from each other with respect to the circular cross-section of said body. The grooves 9 extend approximately from the middle of the conic frustum shaped body of the component 1, that is where the mantle 4 ends, to the ogival tip, which is closed.

Figure 3:
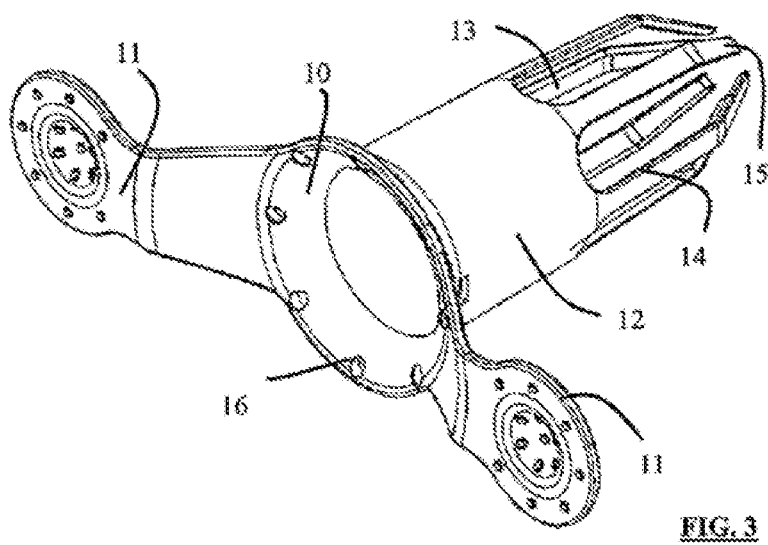
FIG. 3 shows a perspective view of the anoscope.

FIG. 3 shows that the anoscope 2 is a hollow conic frustum shaped body as well, having a flange 10 attached to its mouth. Said flange 10 is provided with at least one handle 11 for handling the anoscope during mounting operations and when in use. Similarly to component 1, also the anoscope 2 has a mantle 12 and an ogival tip provided with a set of parallel longitudinal slots 13 which connect the interior of the anoscope 2 with the surrounding environment. Said slots 13 are equidistant from each other and are separated by lamellar protrusions 14. The number of the lamellar protrusions 14 is the same as the number of the grooves 9 of the component 1, so that, when in use, the protrusions may close or open said slots for connecting the interior of the anoscope 2 with the surrounding environment.

The lamellar protrusions 14, close to their ends, have a curved portion 15 towards the centre in order to tightly fit the ogival tip 6 of the internal component 1. The longitudinal slots 13 of the anoscope 2 are separated from each other by lamellar protrusions 14 which prolong the hollow conic frustum shape of the mantle 12, almost until the ogival tip 6, so that there is an opening between the curved portions of the protrusions 14. Thus, the mantle 12 approximately forms the first half of the anoscope 2 while the lamellar protrusions 14 approximately constitute the second half.

When introducing the component 1 in the anoscope 2, the lamellar protrusions 14, due to their elasticity, slide in the grooves 9 and fill them completely so that respective distal-most ends 1a, 2a of the component 1 and the anoscope 2 exist in the same plane, i.e., a plane that extends transversely with respect to a longitudinal axis "X" of the instrument, as shown in FIG. 1, to form a hollow conic frustum shaped body having a compact and smooth external surface and ending with an ogival tip. Thanks to this smooth and compact external surface, deriving from such peculiar fitting, the composite anoscope of the present invention can be inserted atraumatically in the anal canal.

When the anoscope according to the present invention is used, the lamellar protrusions 14, fitting the grooves 9 of the underlying component 1, prevent the prolapsing ano-rectal mucosa and the rectal muscular tunica from entering the grooves 9. In other words, the lamellar protrusions 14 support the ano-rectal mucosa and the rectal muscular tunica when exploring the injuries while allowing their exact location.

The internal surface of the anoscope 2 is preferably provided with circular and longitudinal markers positioned at predefined intervals. Such markers make it possible to exactly locate the distance of the injuries from the anal margin to thereby perform perfectly focused operations both in longitudinal and circumferential directions.

The flange 10 of anoscope 2 provides a through-holes' pattern 16, suitably equidistant, which can block the anoscope's 2 rotation inside the external component 3, which is provided with suitable posts 17 apted to fit into holes 16 as will be described afterwards.

Figure 4:
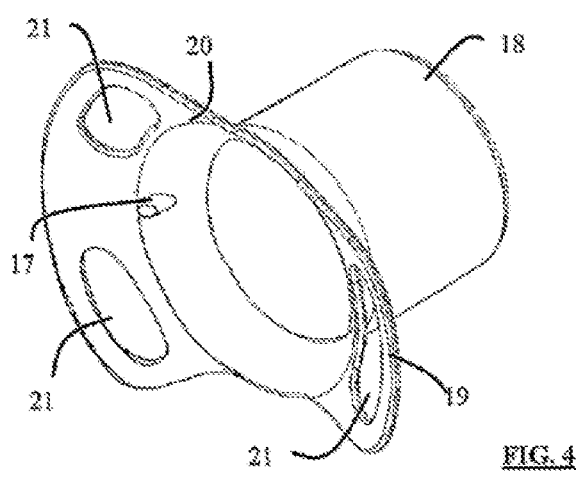
FIG. 4 shows a perspective view of the external component.

Referring now to FIG. 4, the component 3, which is substantially shorter than the other components 1 and 2, is essentially a frustum conic body formed by a mantle 18, provided with slotted wings 19 and 20 attached to its major diameter. Mantle 4 of internal component 1, mantle 12 of anoscope 2, and mantle 18 of external component 3 have substantially the same length, as shown in FIG. 1. Wings 19 and 20 are used as handles and allow the right positioning of the whole composite anoscope inside the anal region. Further, wings 19 and 20 work as a seat in the insertion stroke of the composite anoscope inside the anal canal. This means that wings 19 and 20 have a double function: the first one as handles for the insertion of the anoscope inside the anal canal and the second one as end-stroke seat when the device contacts the anal region.

The slots 21 present in the wings 19 and 20 are used to fix in operation the composite anoscope according to the present invention by suturing external component 3 to perianal skin. Once such fixation has been effected through the above slots, the external component 3 provides both support and axial guide to anoscope 2 and internal component 1.

When anoscope 2 is axially inserted inside component 3, the internal posts 17 thereof fit the through-holes 16 placed on flange 10 of anoscope 2, thus blocking the relative rotation between the two components. In this way the anoscope's 2 angular position is fixed with respect to component 3, thus granting the maintenance of such position during the normal use of the composite anoscope according to the present invention. Obviously, the greater the holes' number on flange 10 and of the respective posts 17 inside the opening of component 3, the finer the degree of regulation of the relative position of anoscope 2 with respect to component 3.

Once the composite anoscope has been fixed to perianal skin by the external component 3, it is possible to axially extract the internal component 1 with handle 7 by disengaging the snapping tongue 8. In this way the inside of anoscope 2 is totally free, thus making it possible to explore the anal and ano-rectal region.

The anoscope according to the present invention is inserted into the anal canal once all of the three components have been tightly inserted into each other so to form one single body provided with an external surface which is smooth and compact, as shown in FIG. 1. After the external component 3 is fixed to the perianal skin by suturing the slotted wings 19 and 20 thereof, the internal component 1 can be removed. Subsequently, it is possible to rotate anoscope 2 inside the cavity of the external component 3 in order to position it so that portions of interest of the mucosa of the rectal wall prolapse into the slots interposed between lamellar protrusions 14. At this stage, anoscope 2 is fixed to the external component 3 by coupling the posts 17 of external component 3 to the holes 16 of flange 10 of anoscope 2. In this way, the anoscope has been tightly positioned inside the anal canal, realizing a fixed reference system during the whole operation. This measure allows making sutures at a proper distance from the anal margin and of a predefined circumferential extent. Further, anoscope 2 can eventually be extracted from the fixed external component 3, anyway leaving the anal canal open in order to introduce other surgical instruments.

Further variations and/or additions may be made by those skilled in the art to the hereinabove described and illustrated embodiments of the invention while remaining within the scope of the same invention. For example, it is obvious that the shape of anoscope's 2 and internal component's 1 handles can change while keeping the same function for the present invention. The same applies to the materials to be used for the construction of the three components or parts thereof. Any suitable material can be used, preferably polyethylene terephthalate.

The invention claimed is:

1. A surgical device comprising:
   an anoscope including a plurality of distally extending protrusions; and
   an internal component adapted to be inserted into the anoscope, the internal component including a plurality of grooves corresponding in configuration and dimensions to the protrusions, whereby the protrusions are positionable within the grooves, such that the device defines a smooth external surface upon insertion of the internal component into the anoscope to a maximum extent permitted by the anoscope.

2. The surgical device of claim 1, wherein the anoscope further includes a mantle, the protrusions extending distally from the mantle.

3. The surgical device of claim 1, wherein the anoscope and the internal component each have a frusto conical configuration, whereby the device defines an ogival distal tip upon insertion of the internal component into the anoscope to the maximum extent permitted by the anoscope.

4. The surgical device of claim 1 further comprising an external component, the anoscope being configured and dimensioned for insertion into the external component.

5. The surgical device of claim 1, wherein the anoscope and the internal component include distalmost surfaces existing in a common plane extending transversely in relation to a longitudinal axis of the device upon insertion of the internal component into the anoscope to the maximum extent permitted by the anoscope.

6. A surgical device comprising:
   an anoscope; and
   an internal component adapted to be inserted into the anoscope, the anoscope and the internal component having corresponding frusto conical configurations cooperatively defining a distal tip of the device upon insertion of the internal component into the anoscope to a maximum extent permitted by the anoscope, the distal tip of the device having an ogival configuration, wherein the anoscope and the internal component include distalmost surfaces existing in a common plane extending transversely in relation to a longitudinal axis of the device upon insertion of the internal component into the anoscope to the maximum extent permitted by the anoscope.

7. An anoscopic device comprising:
   an anoscope; and
   an internal component adapted to be inserted into the anoscope, the anoscope and the internal component being complimentary in configuration and dimensions such that distalmost surfaces of the anoscope and the internal component exist in a common plane extending transversely in relation to a longitudinal axis of the device upon insertion of the internal component into the anoscope to a maximum extent permitted by the anoscope.

8. The anoscopic device of claim 7, wherein the anoscope and the internal component each have a frusto conical configuration.

9. The anoscopic device of claim 7, wherein the anoscope and the internal component are configured and dimensioned such that upon insertion of the internal component into the anoscope to the maximum extent permitted by the anoscope, the internal component forms one single body with the anoscope, the single body exhibiting a smooth external surface.

10. The anoscopic device of claim 9, wherein the single body includes a distal tip having an ogival configuration.

11. The anoscopic device of claim 10 further including an external component, the anoscope being configured and dimensioned for insertion into the external component.

12. The anoscopic device of claim 11, wherein the external component includes a frusto conical shaped mantle, and two wings attached to the mantle, each wing including a plurality of slots.

13. The anoscopic device of claim 12, wherein the wings are attached to the mantle at a location where a transverse dimension defined by the mantle is at a maximum.

14. The anoscopic device of claim 11, wherein the anoscope, the internal component, and the external component each include a hollow body with a circular cross section.

15. The anoscopic device of claim 11, wherein the internal component and the external component include corresponding structure configured and dimensioned for engagement to inhibit relative rotation between the internal component and the external component.

16. The anoscopic device of claim 15, wherein the anoscope includes an anoscope mouth, and an anoscope flange located adjacent the anoscope mouth, the anoscope flange including at least one through hole.

17. The anoscopic device of claim 16, wherein the external component includes a base, and at least one post extending from the base, the at least one post being configured and dimensioned for insertion into the at least one through hole.

18. The anoscopic device of claim 17, wherein the anoscope flange includes a plurality of through holes, and the base of the external component includes a plurality of posts.

19. The anoscopic device of claim 10, wherein the internal component includes an internal component mantle having a plurality of longitudinal grooves extending therefrom that terminate on the distal tip, the plurality of longitudinal grooves extending in parallel relation, and being positioned equidistant from each other.

20. The anoscopic device of claim 19, wherein the anoscope includes an anoscope mantle having a plurality of lamellar protrusions extending therefrom, each lamellar protrusion being configured and dimensioned for positioning within one of the longitudinal grooves.

21. An anoscopic device comprising:
   an anoscope having a body portion with proximal and distal ends, the anoscope including a radially extending flange positioned adjacent the proximal end of the body portion; and
   an internal component having a body portion with proximal and distal ends, the internal component including a radially extending handle positioned adjacent the proximal end of the body portion, the internal component being configured and dimensioned for insertion into the anoscope such that the handle of the internal component abuts the flange of the anoscope, whereupon distalmost surfaces defined by the anoscope and the internal component exist in a common plane extending transversely in relation to a longitudinal axis of the device.

22. The anoscopic device of claim 21, wherein the internal component forms one single body with the anoscope upon abutment of the handle of the internal component with the flange of the anoscope.

23. The anoscopic device of claim 22, wherein the single body formed by the internal component and the anoscope defines a smooth external surface having an ogival tip.

24. The anoscopic device of claim 21 further including an external component having a body portion, the anoscope being configured and dimensioned for insertion into the external component.

25. The anoscopic device of claim 24, wherein the body portion of the anoscope, the body portion of the internal component, and the body portion of the external component are each hollow.

26. The anoscopic device of claim 24, wherein the body portion of the anoscope, the body portion of the internal component, and the body portion of the external component each have a circular cross-sectional configuration.

27. The anoscopic device of claim 24, wherein the internal component and the external component include corresponding structure configured and dimensioned for engagement to inhibit relative rotation between the internal component and the external component.

28. The anoscopic device of claim 27, wherein the flange of the anoscope includes at least one through hole, and the external component includes a base with at least one post configured and dimensioned for positioning within the at least one through hole.

29. The anoscopic device of claim 28, wherein the flange of the anoscope includes a plurality of through holes, and the base of the external component includes a plurality of posts.

30. The anoscopic device of claim 21, wherein the internal component and the anoscope are complimentary in configuration and dimensions.

31. The anoscopic device of claim 30, wherein the distal end of the body portion of the internal component is frusto conical in configuration, and the distal end of the body portion of the anoscope is frusto conical in configuration.

32. The anoscopic device of claim 31, wherein the body portion of the anoscope includes a plurality of distally extending lamellar protrusions.

33. The anoscopic device of claim 32, wherein each lamellar protrusion includes a distal end having a tip bent in relation to a longitudinal axis defined by the body portion of the anoscope.

34. The anoscopic device of claim 33, wherein the tip of each lamellar protrusion extends inwardly towards the longitudinal axis defined by the body portion of the anoscope.

35. The anoscopic device of claim 32, wherein the body portion of the internal component includes a plurality of longitudinal grooves configured and dimensioned to receive a corresponding lamellar protrusion.

* * * * *